United States Patent
Schlussel

(10) Patent No.: US 7,176,343 B2
(45) Date of Patent: Feb. 13, 2007

(54) SCAB PROTECTING BANDAGE

(75) Inventor: Ed Schlussel, 333 Longwood Crossing, Lawrence, NY (US) 11559

(73) Assignee: Ed Schlussel, Lawrence, NY (US)

( * ) Notice: Subject to any disclaimer, the term of this patent is extended or adjusted under 35 U.S.C. 154(b) by 214 days.

(21) Appl. No.: 10/757,014

(22) Filed: Jan. 14, 2004

(65) Prior Publication Data
US 2005/0154340 A1    Jul. 14, 2005

(51) Int. Cl.
A61F 13/00    (2006.01)

(52) U.S. Cl. ........................................ 602/41

(58) Field of Classification Search ............ 602/41–59; 128/888, 889; 424/443–449
See application file for complete search history.

(56) References Cited

U.S. PATENT DOCUMENTS

| | | | |
|---|---|---|---|
| 2,711,739 A * | 6/1955 | Fishbein | 606/215 |
| 3,024,786 A | 3/1962 | Fuzak | |
| 3,625,209 A * | 12/1971 | Clark | 602/44 |
| 3,927,669 A | 12/1975 | Glatt | |
| 4,173,131 A | 11/1979 | Pendergrass et al. | |
| 4,285,338 A | 8/1981 | Lemelson | |
| 4,671,266 A | 6/1987 | Lengyel et al. | |
| 4,726,364 A | 2/1988 | Wylan | |
| 4,832,009 A | 5/1989 | Dillon | |
| 4,917,929 A | 4/1990 | Heinecke | |
| 4,972,829 A | 11/1990 | Knerr | |
| 5,158,555 A | 10/1992 | Porzilli | |
| 5,522,794 A | 6/1996 | Ewall | |
| 5,522,810 A | 6/1996 | Allen, Jr. et al. | |
| 5,571,080 A | 11/1996 | Jensen | |
| 5,593,395 A | 1/1997 | Martz | |
| 5,676,967 A | 10/1997 | Williams et al. | |
| 5,843,018 A | 12/1998 | Shesol et al. | |
| 5,902,260 A | 5/1999 | Gilman | |
| 6,191,338 B1 | 2/2001 | Haller | |
| 6,267,744 B1 | 7/2001 | Roberts et al. | |
| 6,362,388 B1 | 3/2002 | Lucas | |
| 6,495,229 B1 | 12/2002 | Carte et al. | |
| 2002/0062097 A1 | 5/2002 | Simpson | |

FOREIGN PATENT DOCUMENTS

| | | |
|---|---|---|
| EP | 1059325 A2 | 12/2000 |
| GB | 1 581 295 | 12/1980 |
| GB | 2089850 A | 6/1982 |
| WO | WO 97/34553 | 9/1997 |

OTHER PUBLICATIONS

DelSta Ttechnologies, Inc. Delnet Apertured Film.*

* cited by examiner

Primary Examiner—Henry Bennett
(74) Attorney, Agent, or Firm—Gottlieb, Rackman & Reisman

(57) ABSTRACT

An improved bandage for application to a wound scab is provided. The bandage comprises a bandage strip defined by a material having an air porosity of at least 50 cubic ft./min./sq. ft. The strip includes three sections, two end sections and a middle section, all of which are preferably made from one continuous integrally formed porous material. The end sections have an adhesive which is applied to the underlying portion thereof to enable the bandage strip to be fixedly positioned over a wound scab. The central section, which is applied over the wound scab itself, solely comprises the porous strip material.

15 Claims, 2 Drawing Sheets

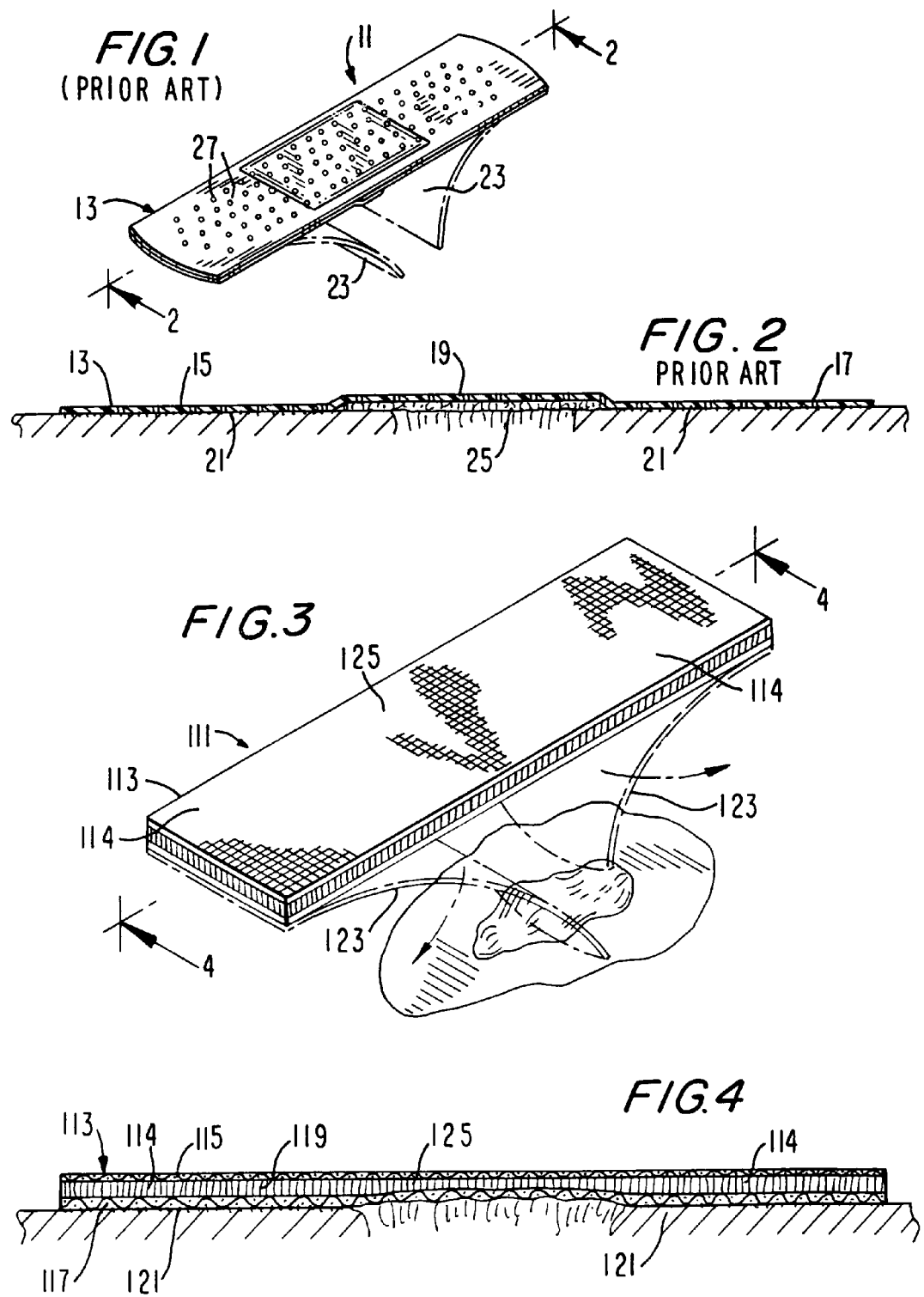

SCAB PROTECTING BANDAGE

BACKGROUND OF THE INVENTION

The invention relates to a scab protecting bandage, and more particularly to a bandage which protects a scab that is formed over a wound in order to facilitate healing by enhancing air exposure while at the same time protecting the scab from injury.

Prior art wound coverings normally have some type of padding to protect the wound as well as some type of medicine that is applied to the bottom of the padding for application to the wound when the wound covering is applied thereto. For example, as depicted in FIGS. 1 and 2, a conventional wound bandage 11 is constructed of a waterproof plastic film strip 13 having end sections 15 and 17 and a central section 19. End sections 15 and 17 have an adhesive coating applied along the underlying portions thereof. Central portion 19 has a gauze or mesh like material disposed along the underlying portion 25 that is suitable for covering a wound. Strip 13 preferably includes a plurality of perforations 27 for enhancing air flow through gauze or mesh like material 25.

In order to apply bandage 11 to a wound, a pair of release paper strips 23 are disposed along the underlying portion of film strip 13. Release paper strips 23 are made of a plastic material such as polyethylene and protect bandage 11 from any damage prior to use. Release paper strips 23 are peeled away, as shown in FIG. 1, in order to expose coated adhesive 21 and gauze or mesh like material 25, as is well known. When applied to an individual's skin surface, gauze or mesh like material 25 is laid over the wound while end portions 15 and 17, utilizing coated adhesive 21, are laid over and adhesively applied to the individual skin in order to secure bandage 11.

While a bandage 11 made in accordance with the prior art is helpful in protecting a fresh wound from injury, and is also helpful in facilitating the healing thereof, such a bandage is less than desirable once the wound forms a scab. For a scab to heal as efficiently as possible, it is important to provide as much air flow to the scab area as possible. However, because bandage 11 of the prior art is defined by a plastic strip or sheet 13, air flow to a scab, even with the presence of perforations 27, is significantly inhibited. And while air flow would be maximized to a scab if no bandage were applied at all, such a situation substantially increases the risk of scab injury and the reforming of a wound.

Accordingly, it would be desirable to provide a bandage which overcomes these disadvantages.

SUMMARY OF THE INVENTION

Generally speaking, in accordance with the invention, an improved bandage for application to a wound scab is provided. The bandage comprises a bandage strip defined by a material having an air porosity of at least 50 cubic ft./min./sq. ft. The strip preferably includes three integrally formed sections, two end sections and a middle section, and is made of a single porous material. The end sections have an adhesive which is applied to the underlying portion thereof to enable the bandage strip to be fixedly positioned over a wound scab. The central section, which is applied over the wound scab itself, solely comprises the porous strip material.

Any size and shape scab protecting bandage made in accordance with the invention may be constructed. The bandage strip of the inventive bandage may be made from fabric materials providing maximum porosity, including knitted netting or mesh, woven netting or mesh, fine tricot fabric, double needle bar cushioned fabric, or any other fabric material which can be formed into a strip bandage and which facilitates maximum air porosity therethrough.

Preferably, the porous material defining the bandage strip has an air porosity of at least 150 cubic ft./min./sq. ft. More preferably, the air porosity is at least 250 cubic ft./in./sq. ft. Even more preferably, the air porosity is at least 500 cubic ft./min./sq. ft. In contrast, a conventional wound bandage, such as that depicted in FIGS. 1 and 2, discussed hereinbefore, typically has an air porosity of no greater than 20 cubic ft./min./cubic ft.

Accordingly, it is an object of the invention to provide an improved bandage structure.

A main object of the invention is to provide a bandage product specifically designed for facilitating wound scab healing.

Yet a further object of the invention is to provide a bandage product having the characteristics of enhanced air porosity.

Still other objects and advantages of the invention will, in part, be obvious and will, in part, be apparent from the following description.

BRIEF DESCRIPTION OF THE DRAWINGS

For a fuller understanding of the invention, reference is made to the following description, taken in connection with the accompanying drawings, in which:

FIG. 1 is a perspective view of a bandage made in accordance with the prior art;

FIG. 2 is a cross-sectional view taken along line 2—2 of FIG. 1;

FIG. 3 is a perspective view of a bandage made in accordance with the invention and constructed of a spacer fabric material;

FIG. 4 is a cross-sectional view taken along line 4—4 of FIG. 3;

DETAILED DESCRIPTION OF THE PREFERRED EMBODIMENTS

Figure 5:
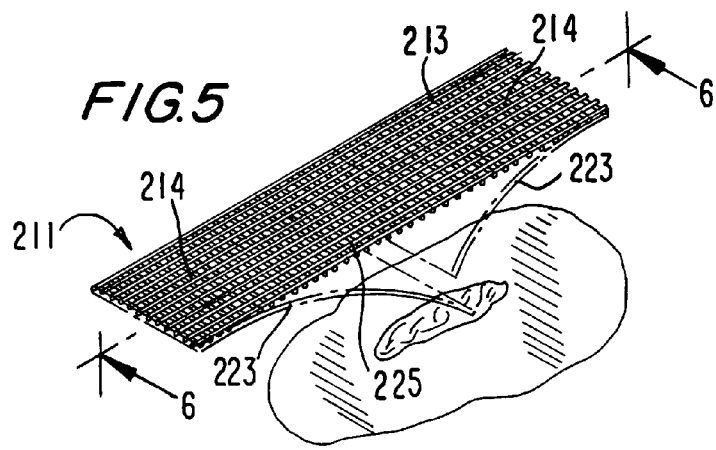
FIG. 5 is a perspective view of a bandage made in accordance with the invention and constructed of a mesh fabric material.

Referring now to FIGS. 3 and 4, a bandage 111 made in accordance with the invention is shown defined by a strip 113 made of a double needle-bar spacer fabric material having an air porosity of preferably between 50 and 500 cubic ft./min./sq. ft., and more preferably between 150 and 500 cubic ft./min./sq.ft. Strip 113 is comprised of end sections 114 and a central section 125. Strip 113 is defined by a first yarn layer 115 made of any type of synthetic or natural fiber, a second yarn layer 117 made of any type of synthetic or natural fiber and interconnecting yarns 119 made of monofilament yarns running therebetween. End sections 114 have an adhesive coating 121 applied along the underlying portions thereof. This facilitates the application of release paper 123, which is made of plastic film or paper and is selectively peeled away prior to application of bandage 111 to a wound scab. When applied, the central section 125 of bandage strip 113 is positioned over the wound scab while end sections 114, which are coated with adhesive along the underside thereof, are applied along the skin of the user away from the wound scab.

Figure 6:
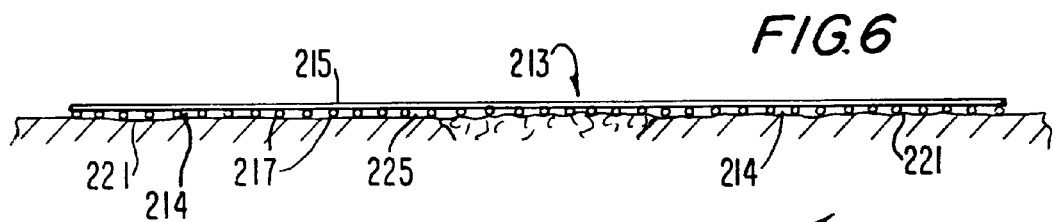
FIG. 6 is a cross-sectional view taken along line 6—6 of FIG. 5.

In FIGS. 5 and 6, an alternative bandage made in accordance with the invention and generally indicated at 211 is shown. Bandage 211 is defined by a strip made of a mesh fabric material 213 made from yarns having a fineness of 15 to 500 denier and an air porosity of at least 50 cubic ft./min./sq.ft., preferably at least 250 cubic ft./min./sq.ft., and more preferably of at least 500 cubic ft./min./sq. ft. Mesh fabric strip 213 is made of a woven, knitted or molded material and includes end sections 214, which have adhesive 221 applied along the undersides thereof, and a central section 225. Mesh fabric strip 213 includes a plurality of longitudinally extending yarns 215 and a plurality of transversely extending yarns 217, which together define a grid type woven mesh netting or an interconnected grid of longitudinal, transverse and diagonal yarns which form a knitted mesh, or a porous tricot fabric composed of natural or synthetic yarns. Yarns 215 and 217 are made from any yarn like material. Before applying bandage 211 to a wound scab, release paper 223 is peeled away from the underside of mesh fabric strip 213. Central section 225 of strip 213 is applied over the wound scab, while end sections 214 are adhered to the wearer's skin away from the wound scab.

Figure 7:
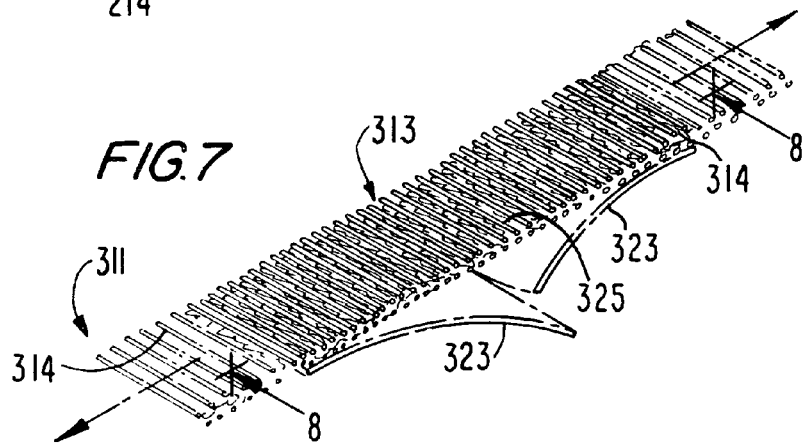
FIG. 7 is a perspective view of a bandage made in accordance with the invention and constructed of a stretchable woven or knitted gauze.
Figure 8:
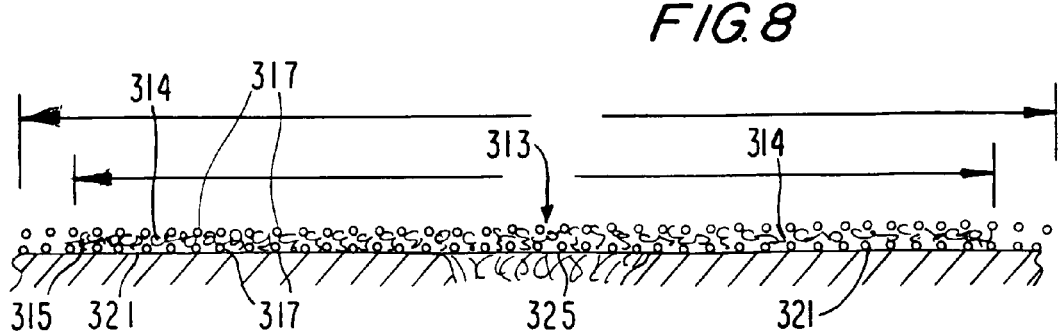
FIG. 8 is a cross-sectional view taken along line 8—8 of FIG. 7.

In FIGS. 7 and 8, a further version of a bandage made in accordance with the invention and generally indicated at 313 is shown. Bandage 313 is defined by a bandage strip 313 made of a woven gauze material having an air porosity of at least 50 cubic ft./min./sq.ft. and preferably of at least 250 cubic ft./min./sq. ft. Strip 313, as before, includes end portions 314 having an adhesive 321 coated along the underlying portions thereof and a central section 325. Strip 313 includes at least two layers of a plurality of a transversely extending yarns 317 made from any yarn-like material or stretchable yarn and a layer of stretchable longitudinally extending yarns 315 made from elastomeric or stretch yarns of woven substrate. Another form would be interconnected longitudinal, transverse and diagonal yarns, or combination fabrics made of knitted and woven components within fabric mesh. As before, in order to apply bandage 311 to a wound scab, release papers 323 are peeled away from the underside of end sections 314. Central section 325 is then positioned over the wound scab and the adhesive sides of end portions 314 are adhered to the individual skin away from the wound scab. Significantly, since strip 313 is transversly and/or longitudinally stretchable, as shown in FIG. 8, central section 325 may be adjusted in size in a transverse and/or longitudinal direction in order to accommodate various size and location sites of wound scabs, such as those over joints.

As stated hereinabove, the three section bandage strip of the invention is preferably made of a single integrally formed porous material. Another version, though more complicated to manufacture and thus less economical, could be made of three sections with the two end sections made of a different material than, and fused or sewn to, the middle section.

Any of the above described bandage products can be produced from a mono or multi-filament yarn, a stretch or elastic material, synthetic or natural fibers, and/or extruded or molded materials.

It will thus be seen that the objects set forth above, and those made apparent from the preceding description, are efficiently attained, and since certain changes may be made in the products set forth above without departing from the spirit and scope of the invention, it is intended that all matter contained in the above description and shown in the accompanying drawing shall be interpreted as illustrative and not in a limiting sense.

It is also to be understood that the following claims are intended to cover all the generic and specific features of the invention herein described, and all statements of the scope of the invention, which, as a matter of language, might be said to fall therebetween.

The invention claimed is:

1. A bandage comprising:
   a strip having a facing surface and a back surface and defined by a pair of end portions and a central portion with the central portion sized to overly a wound;
   an adhesive substantially covering only said facing surfaces of said end portions;
   wherein at least said central portion of said strip is made of a material having an air porosity of at least 50 cubic ft./min./sq. ft. and is selected from the group consisting of a mesh and a gauze, said material including at least one of a plurality of longitudinally extending yarns, a plurality of transversely extending yarns, and a plurality of diagonally extending yarns.

2. The bandage of claim 1, wherein said end portions and said central portion are integrally formed of said material.

3. The bandage of claim 2, wherein said material comprises a fabric material.

4. The bandage of claim 3, wherein the fabric is one of knitted, woven, or molded.

5. The bandage of claim 1, further including release paper elements overlyingly adhered to said end portions of said strip along said facing surface thereof and selectively peelable therefrom.

6. A bandage comprising:
   a strip having a facing surface and a back surface and defined by a pair of end portions and a central portion with the central portion sized to overly a wound;
   an adhesive substantially covering only said facing surfaces of said end portions;
   wherein at least said central portion of said strip is made of a material having an air porosity of between 50 and 500 cubic ft./min./sq. ft. and is a spacer fabric material comprising a first yarn layer, a second yarn layer, and a plurality of yarns running therebetween.

7. The bandage of claim 3, wherein said fabric material comprises a mesh material.

8. The bandage of claim 7, wherein said mesh material has an air porosity of at least 250 cubic ft./min./sq. ft.

9. The bandage of claim 3, wherein said fabric comprises a gauze material.

10. The bandage of claim 9, wherein said gauze material has an air porosity of at least 250 cubic ft./min./sq. ft.

11. The bandage of claim 10, wherein said gauze material includes at least two layers of a plurality of transversely extending yarns.

12. The bandage of claim 7, wherein said mesh material has a fineness of between 15 and 500 denier.

13. The bandage of claim 6, wherein said air porosity is between 150 and 500 cubic ft./min./sq.ft.

14. The bandage of claim 6, wherein said plurality of yarns are mono filament.

15. The bandage of claim 6, further including release paper elements overlying adhered to said end portions of said strip along said facing surface thereof and selectively peelable therefrom.

* * * * *